United States Patent [19]
Esch et al.

[11] Patent Number: 5,627,198
[45] Date of Patent: May 6, 1997

[54] HETEROCYCLIC AMIDES

[75] Inventors: Peter Esch, Linz; Robertson Towart, Pasching; Franz Rovenszky, Linz, all of Austria

[73] Assignee: Hafslund Nycomed Pharma Aktiengesellschaft, Austria

[21] Appl. No.: 567,057

[22] Filed: Dec. 4, 1995

[30] Foreign Application Priority Data

Dec. 5, 1994 [AT] Austria ................................ 2252/94

[51] Int. Cl.⁶ .................. C07D 285/135; A61K 31/425
[52] U.S. Cl. .................. 514/363; 514/371; 514/444; 514/445; 514/447; 548/139; 548/195; 549/59; 549/63; 549/64
[58] Field of Search .................. 548/134, 195; 544/59, 63, 69; 514/363, 371, 444, 445, 447

[56] References Cited

FOREIGN PATENT DOCUMENTS

0524781A1  1/1993  European Pat. Off. .
0617010A1  9/1994  European Pat. Off. .

OTHER PUBLICATIONS

K.E. Andersson, *Pharmacol. Rev.*, 45, 253–308 (1993).

K.E. Andersson, *Drugs*, 35, 477–494 (1988).

*Primary Examiner*—Robert Gerstl
*Attorney, Agent, or Firm*—Wenderoth, Lind & Ponack

[57] ABSTRACT

The invention relates to heterocyclic amides of the formula

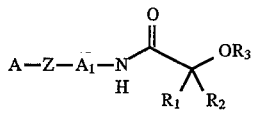

in which the radicals A, Z, $A_1$, $R_1$, $R_2$ and $R_3$ are as defined in the description, to a process for the preparation of these amides and to their use as active substances for the curing and amelioration of disorders and diseases which can be treated by exerting influence on potassium channels.

12 Claims, No Drawings

HETEROCYCLIC AMIDES

The invention relates to novel heterocyclic amides which can be employed as active substances against disorders and diseases which are cured or ameliorated by exerting influence on potassium channels.

It is known that uncontrolled or unstable muscle spasms of the bladder muscle can lead to urinary incontinence. Although the parasympathetic system plays a large role in the controlled, physiological functioning of the bladder in humans, uncontrolled discharges of urine can more often be attributed to oversensitivity of the urinary tract smooth muscle (K. -E. Andersson, Pharmacology of lower urinary tract smooth muscles and penile erectile tissue, Pharmacol. Rev. 45, 253–308, 1993). Certain medicaments, for example spasmolytics, calcium antagonists and potassium channel activators, are able to suppress this oversensitivity. Some of them have already been employed in practice as prophylactics against urinary incontinence (K. -E. Andersson, Current concepts in the treatment of disorders of micturition, Drugs 35, 477–494, 1988). The disadvantage of all of these compounds described therein is their pronounced profile of side-effects, which include, inter alia, cardiovascular and gastrointestinal disorders (ibid.).

EP-A 0 524 781 discloses substituted amides which bring about the opening of potassium channels. These substituted amides contain as substituents a substituted or unsubstituted phenyl or pyridyl radical. EP-A 0 617 010 discloses similarly active amides which contain as substituents a substituted or unsubstituted phenyl, pyridyl, pyrimidyl, pyridazinyl or pyrazinyl radical.

The object of the present invention was to provide novel compounds which possess outstanding activity in exerting influence on potassium channels and a high selectivity coupled with reduced side-effects, and which are therefore superior to the known compounds.

Unexpectedly, it has been possible to achieve this object by the provision of novel heterocyclic amides which contain as heteroaromatic substituent a ring comprising sulfur or comprising sulfur and nitrogen.

The invention accordingly provides heterocyclic amides of the formula I

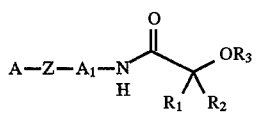

in which

A is an aromatic or S- or N-heteroaromatic ring having 5–10 carbon atoms which can be unsubstituted or mono- or polysubstituted by straight-chain or branched $Cl_1$–$C_4$ alkyl, $Cl_1$–$C_4$ alkoxy, hydroxyl, halogen or $CF_3$, $CF_3CF_2$, Z is a radical C=O, SO or $SO_2$, $A_1$ is a heteroaromatic system of the formula IIa–IIc

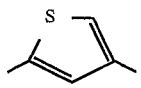

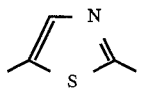

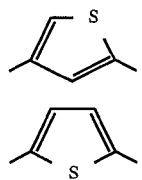

or a heteroaromatic system of the formula IIIa–IIIc

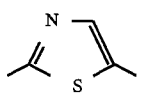

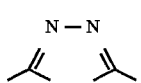

$R_1$ and $R_2$ independently of one another are H, straight-chain or branched ($C_1$–$C_4$)-alkyl or fluorinated alkyl, and $R_3$ is H, straight-chain or branched ($C_1$–$C_4$)-alkyl or a group which can be eliminated under physiological conditions.

The compounds of the formula I can exist as a mixture of their optical isomers or else in each case in enantiomerically pure form. Both mixtures of the optical isomers of the compounds of the formula I and the respective enantiomerically pure form are provided by the present invention.

In the formula I, the radical A is an aromatic or S- or N-heteroaromatic ring having 5–10 carbon atoms, for example a phenyl radical, a thienyl radical, a pyridyl radical, a pyrimidyl radical, a pyridazinyl radical or an imidazolyl radical. These radicals can be unsubstituted or mono- or polysubstituted, for example by straight-chain or branched $C_1$–$C_4$ alkyl, such as methyl, ethyl, propyl, isopropyl, butyl, isobutyl or t-butyl, or by straight-chain or branched $C_1$–$C_4$ alkoxy, for example methoxy, ethoxy, propoxy or butoxyradicals. Furthermore, this heteroaromatic ring can be mono- or polysubstituted by hydroxyl, halogen, such as chlorine, fluorine or bromine, or by the radicals $CF_3$, $CF_3CF_2$.

Preferred compounds are those in which the radical A is phenyl, phenyl monosubstituted by halogen, preferably chlorine or fluorine, or by $CF_3$, $CF_3CF_2$, or is 2- or 3-thienyl.

Particularly preferred compounds are those in which the radical A is phenyl which is unsubstituted or substituted by halogen.

The radical Z is a carbonyl group C=O, a sulfinyl group SO or a sulfonyl group $SO_2$.

Preferred compounds are those in which the radical Z is a carbonyl group or a sulfonyl group.

The radical $A_1$ is a heteroaromatic system of the formulae IIa–IIc

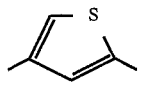

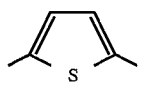

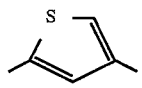

or a heteroaromatic system of the formula IIIa–IIIc

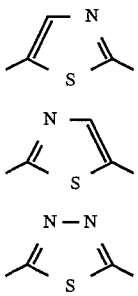

Preferred compounds are those in which the radical $A_1$ is a heteroaromatic system of the formula IIb, IIIb or IIIc.

Particularly preferred compounds are those in which the radical $A_1$ is a heteroaromatic system of the formula IIb.

The radicals $R_1$ and $R_2$ are independently of one another H, a straight-chain or branched $C_1$–$C_4$-alkyl radical, for example a methyl, ethyl, propyl, isopropyl, butyl, isobutyl or t-butyl radical, or a fluorinated alkyl radical, for example the radical $CF_3$ or $CF_3CF_2$.

Preferred compounds are those in which the radicals $R_1$ and $R_2$ independently of one another are a straight-chain or branched $C_1$–$C_4$-alkyl radical or the radical $CF_3$.

Particularly preferred compounds are those in which the radicals $R_1$ and $R_2$ independently of one another are a methyl radical or the radical $CF_3$.

The radical $R_3$ is H, straight-chain or branched alkyl having 1–4 carbon atoms, i.e. a methyl, ethyl, propyl, isopropyl, butyl, isobutyl or t-butyl radical, or a group which can be eliminated under physiological conditions. Examples of such groups which can be eliminated under physiological conditions are the radical CON, acetyl or acetylalkyl radicals.

The invention additionally provides a process for the preparation of compounds of the formula I

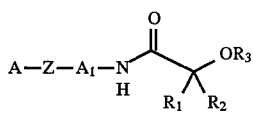

by coupling a compound of the formula IV

using known coupling reagents, with a compound of the formula V

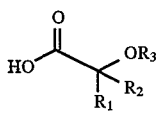

and, if appropriate, separating the resulting mixture of optical isomers into the enantiomers.

The compounds of the formula V can also be employed in one of their optically active forms, in which case the product obtained is in each case the enantiomerically pure form of a compound of the formula I.

Compounds of the formulae IV and V are known from the literature or can be prepared by methods familiar to the person skilled in the art.

The coupling reagents used are, for example, coupling reagents which are known from peptide synthesis, examples being $SOCl_2$, DCC, N,N-carbonyldiimidazole and the like.

In order to carry out the process, a compound of the formula IV is brought into contact, in a suitable diluent, with a coupling reagent, for example thionyl chloride, DCC or N,N-carbonyldiimidazole. Suitable diluents are diluents or solvents which are inert under reaction conditions, for example N,N-dimethylacetamide, dimethylformamide or tetrahydrofuran and the like. The reaction temperature is dependent on the choice of coupling agent and can vary between –25° C. and 100° C. A compound of the formula V is then added and the mixture is reacted at a temperature of from –25° C. to 100° C., preferably at room temperature.

The reaction product obtained is subsequently isolated by extraction and stripping of the solvent, and if desired can be purified further by known methods, for example by recrystallization or chromatography.

The resolution of the reaction products, which may be present in the form of a mixture of the optical isomers, takes place by methods familiar to the person skilled in the art, for example by coupling with (1S)-(–)-camphanic acid chloride or with (R)-(+)-methylbenzyl isocyanate, after which the diastereomers thus obtained are separated by conventional methods, for example by crystallization or chromatography, and the protecting groups are eliminated.

The compounds according to the invention exhibit outstanding activity in exerting influence on potassium channels, coupled with reduced side-effects. They show high selectivity in those disorders and diseases of the bladder and of the efferent urinary tract passages which can be cured or ameliorated by exerting influence on potassium channels.

Because of these pharmacological properties, the novel compounds can be used, alone or mixed with other active substances, in the form of customary pharmaceutical preparations, as medicaments for the treatment of disorders or diseases which can be cured or ameliorated by exerting influence on the potassium channels.

The invention additionally provides medicaments which are used, for example, in the form of pharmaceutical preparations and which comprise the compounds of the formula (I) according to the invention and their salts as a mixture with a pharmaceutical, organic or inorganic excipient which is suitable for oral, enteral, parenteral and topical administration, examples of such excipients being water, gelatin, gum arabic, lactose, starch, magnesium stearate, talc, vegetable oils, polyalkylene glycols, petroleum jelly and the like.

The pharmaceutical preparations can be in solid form, for example as tablets, film-coated tablets, other coated tablets, suppositories, capsules or microcapsules or in liquid form, for example as solutions, injection solutions, suspensions or emulsions, or in compositions with delayed release of the active substance. If desired, they can be sterilized and/or they comprise auxiliaries such as preservatives, stabilizers or emulsifiers, or salts for modifying the osmotic pressure, or buffers.

In particular, pharmaceutical preparations can comprise the compounds according to the invention in combination with other therapeutically useful substances. The compounds according to the invention can be formulated with these substances together with the abovementioned auxiliaries and/or excipients to give combined preparations.

The novel compounds can be present in the compositions according to the invention in a proportion of 0.1–200 mg per tablet, the remainder being a pharmaceutically acceptable filler.

A suitable dose for administration of the compounds is about 0.01–100 mg/kg per day, although other doses are suitable depending on the condition of the patient to be treated. The novel compounds can also be administered in a plurality of doses.

EXAMPLE 1

N-[5-(Phenylcarbonyl) thien-2-yl]-3,3,3-tri-fluoro-2-hydroxy-2-methylpropanamide Thionyl chloride (110 µl, 1.51 mmol) is added to 3,3,3-trifluoro-2-hydroxy-2-methylpropanoic acid (240 mg, 1.52 mmol) in 5 ml of N,N-dimethylacetamide at −15°/−10° C., and the mixture is stirred at this temperature for one hour. Then 2-amino-5-(phenylcarbonyl) thiophene (200 mg, 0.983 mmol) is added and the reaction mixture is equilibrated to room temperature. After the reaction has ended, the reaction mixture is poured into 200 ml of water and subjected to extraction with 3×100 ml of ethyl acetate. The combined organic phases are dried over magnesium sulfate and filtered and the solvent is distilled off. The orange-colored oil which remains is purified by flash chromatography (eluent: 50% v/v ethyl acetate in petroleum ether (40/60)).

Yield: 290 mg of N-[5-(phenylcarbonyl)thien-2-yl]-3,3,3-trifluoro-2-hydroxy-2-methylpropanamide (86% of theory) as pale yellow crystals.

M.p.: 169°–170° C. $^1$H NMR (400 MHz, CDCl$_3$) 1.74 (s, 3H), 6.89 (d, J=4.0 Hz, 1H), 7.41–7.46 (m, 2H), 7.48 (d, J=4.0 Hz, 1H), 7.51–7.56 (m, 1H), 7.73–7.78 (m, 2H), 10.02 (s, 1H). $^{13}$C NMR (100 MHz CDCl$_3$) 20.0, 75.6 (q, $^2J_{C,F}$=30.2 Hz), 114.5, 123.9 (q, $^1J_{C,F}$=285.8 Hz), 128.5, 129.0, 132.2, 134.6, 134.7, 138.0, 147.3, 166.3, 189.5.

The synthesis of 3,3,3-trifluoro-2-hydroxy-2-methylpropanoic acid is described by R. A. Darrall, F. Smith, M. Stacey and J. C. Tatlow J. Chem. Soc. 1951, 2329.

The starting compound is prepared as follows:
5-(Phenylcarbonyl)thiophene-2-carboxylic acid:

A 1.6M solution of n-butyllithium in n-hexane (51.0 ml, 81.3 mmol) is added dropwise to diisopropylamine (11.6 ml, 82.2 mmol) in 150 ml of absolute THF at −70° C. After stirring at −70° C. for 15 minutes, thiophene-2-carboxylic acid (5.00 g, 39.0 mmol) is added and the mixture is held at −70° C. After 45 minutes benzonitrile (5.0 ml, 49 nunol) is added dropwise and the mixture is stirred at −70° C. for 90 minutes. After equilibration to room temperature, the reaction mixture is poured into 200 ml of water and subjected to extraction with 200 ml of ether, and this organic phase is discarded. The aqueous phase is adjusted to a pH of 2 using a 6N HCl solution and is subjected to extraction with 2×200 ml of ether. The combined organic phases are dried over magnesium sulfate and the solvent is distilled off. The residue is suspended in 50 ml of 6N HCl solution and the suspension is heated at 80° C. for one hour. The precipitated crystals are filtered off and dried under vacuum overnight.

Yield: 8.3 g of 5-(phenylcarbonyl) thiophene-2-carboxylic acid (92% of theory) as pale yellow crystals.

M.p.: 176°–177° C.

$^1$H NMR (400 MHz, DMSO-d$_6$) 7.55–7.63 (m, 2H), 7.68–7.75 (m, 1H), 7.70 (d, J=3.9 Hz, 1H), 7.77 (d, J=3.9 Hz, 1H), 7.83–7.90 (m, 2H). $^{13}$C NMR (100 MHz, DMSO-d$_6$) 128.9, 129.1, 133.2, 133.5, 135.2, 136.8, 141.4, 146.8, 162.5, 187.7.

tert-Butyl [5-(phenylcarbonyl) thien-2-yl]carbamate:

Triethylamine (0.72 ml, 5.2 mmol) and diphenylphosphoryl azide (1.1 ml, 5.1 mmol) are added to 5-(phenylcarbonyl)-thiophene-2-carboxylic acid (0.99 g, 4.3 mmol) in 40 ml of absolute tert-butanol. The reaction mixture is boiled under reflux for 5 hours. The solvent is distilled off. The residue is taken up in ethyl acetate and washed with water. The organic phase is dried over magnesium sulfate and filtered and the solvent is distilled off. The solid which remains is purified by flash chromatography (eluent: 25% v/v ethyl acetate in petroleum ether (40/60)).

Yield: 400 mg of tert-butyl [5-(phenylcarbonyl) thien-2-yl]carbamate (31% of theory) as orange crystals.

M.p.: 185°–186° C.

$^1$H NMR (400 MHz, CDCl$_3$) 1.54 (s, 9H), 6.58 (d, J=4.2 Hz, 1H), 7.43 (d, J=4.2 Hz, 1H), 7.43–7.48 (m, 2H), 7.52 (bs, 1H), 7.50–7.55 (m, 1H), 7.78–7.82 (m, 2H). $^{13}$C NMR (100 MHz, CDCl$_3$) 28.2, 82.7, 111.1, 128.3, 128.9, 131.6, 133.6, 134.5, 138.6, 150.1, 151.6, 188.1.

2-Amino-5-(phenylcarbonyl) thiophene:

tert-Butyl [5-(phenylcarbonyl) thien-2-yl]carbamate (0.30 g, 0.99 mmol) is dissolved in 5 ml of trifluoroacetic acetic acid and the solution is stirred at room temperature for 2 hours. The trifluoroacetic acid is distilled off and the residue is partitioned between semisaturated sodium hydrogen carbonate solution and dichloromethane. The phases are separated and the aqueous phase is subjected to extraction with dichloromethane. The combined organic phases are dried over potassium carbonate and filtered and the solvent is distilled off.

Yield: 0.20 g of 2-amino-5-(phenylcarbonyl)thiophene (99% of theory) as red crystals.

$^1$H NMR (400 MHz, DMSO-d$_6$) 5.99 (d, J=4.3 Hz, 1H), 7.18 (bs, 2H), 7.23 (d, J=4.3 Hz, 1H), 7.45–7.60 (m, 3H), 7.62–7.67 (m, 2H).

EXAMPLE 2

N-[5-(Phenylcarbonyl)thiazol-2-yl]-3,3,3-trifluoro-2-hydroxy-2-methylpropanamide Thionyl chloride (80 µl, 1.1 mmol) is added to 3,3,3-trifluoro-2-hydroxy-2-methylpropanoic acid (150 mg, 0.949 mmol) in 5 ml of N,N-dimethylacetamide at −15°/−10° C. and the mixture is stirred at this temperature for one hour. After addition of 2-amino-5-(phenylcarbonyl)thiazole (130 mg, 0.636 mmol) and equilibration to room temperature, the reaction mixture is stirred for 2.5 hours, then poured into 100 ml of water and subjected to extraction with 3×100 ml of ethyl acetate. The combined organic phases are washed with 50 ml of saturated sodium chloride solution, dried over magnesium sulfate and filtered, and the solvent is distilled off. The oil which remains is purified by flash chromatography (eluent: 33% v/v ethyl acetate in petroleum ether (40/60)) to give N-[5-(phenylcarbonyl)thiazol-2-yl]-3,3,3-trifluoro-2-hydroxy-2-methylpropanamide (0.10 g, 46%) as pale yellow crystals. These crystals are digested in dichloromethane.

Yield: 50 mg of the title compound as white crystals.

M.p.: 193°–194° C.

$^1$H NMR (400 MHz, DMSO-d$_6$) 1.62 (s, 3H), 7.56–7.61 (m, 3H), 7.67–7.72 (m, 1H), 7.84–7.88 (m, 2H), 8.17 (s, 1H).

The starting compound is prepared as follows:
tert-Butyl thiazol-2-ylcarbamate:

2-Aminothiazole (5.00 g, 49.9 mmol) and di-tert.butyl pyrocarbonate (23.0 ml, 100 mmol) in 250 ml of absolute methanol are boiled under reflux for 2 hours. In addition, di-tert-butyl pyrocarbonate (11.5 ml, 50.1 mmol) is added dropwise and the mixture is boiled under reflux for a further 2 hours. The reaction mixture is taken up in 250 ml of methanol and stirred with activated carbon, the mixture is filtered and the activated carbon is washed with dichloromethane. After evaporating off the solvents from the combined organic phases, the residue is digested with hexane.

Yield: 9.41 g of tert-butyl thiazol-2-ylcarbamate (94% of theory) as pale yellow crystals.

M.p.: 178°–179° C. (hexane).

$^1$H NMR (400 MHz, DMSO-d$_6$) 1.48 (s, 9H), 7.13 (d, J=3.8 Hz), 1H), 7.35 (d, J=3.8 Hz, 1H). $^{13}$C NMR (100 MHz, DMSO-d$_6$) 28.0, 81.1, 112.9, 137.9, 152.9, 159.9.

[tert-Butyl [5-(phenylcarbonyl)thiazol-3-yl]carbamate:

A 1.6M solution of n-butyllithium in n-hexane (6.90 ml, 11.0 mmol) is added dropwise to diisopropylamine (1.55 ml, 11.0 mmol) in 100 ml of absolute THF at −70° C. After stirring at −70° C. for 30 minutes, tert-butyl thiazol-2-ylcarbamate (1.00 g, 4.99 mmol) is added and the mixture is held at −70° C. After 60 minutes, benzo-nitrile (0.60 ml, 5.9 mmol) is added dropwise and the mixture is stirred at −70° C. for 60 minutes. After equilibration of the reaction mixture to room temperature, it is stirred for 2 hours. The reaction mixture is poured into 300 ml of semisaturated ammonium chloride solution and subjected to extraction with 4×100 ml of dichloromethane. The combined organic phases are dried over magnesium sulfate and filtered and the solvent is distilled off. The crude product (1.40 g) is suspended in 150 ml of ether, and 100 ml of 0.1N HCl solution are added. The mixture is boiled under reflux for 1.5 hours. The reaction mixture is taken up in 100 ml of 0.1N HCl solution and subjected to extraction with 4×100 ml of dichloromethane. The combined organic phases are dried over magnesium sulfate and filtered and the solvent is distilled off.

Yield: 1.15 g of tert-butyl [5-(phenylcarbonyl) thiazol-2-yl]carbsunate (76% of theory) as yellow crystals.

M.p.: 232°–233 ° C. (decomposition).

$^1$H NMR (400 MHz, CDCl$_3$+10% DMSO-d$_6$) 1.36 (s, 9H), 7.26–7.32 (m, 2H), 7.36–7.41 (m, 1H), 7.58–7.63 (m, 2H), 7.68 (s, 1H), 11.26 (bs, 1H). $^{13}$C NMR (100 MHz, CDCl$_3$+10% DMSO-d$_6$) 28.1, 82.7, 128.4, 128.5, 131.8, 132.1, 138.1, 146.7, 152.5, 166.6, 187.4.

2-Amino-5-(phenylcarbonyl)thiazole:

tert-Butyl-5-(phenylcarbonyl)thiazol-2-yl]carbamate (0.82 g, 2.70 mmol) is dissolved in 25 ml of trifluoroacetic acid and the solution is stirred at room temperature for 1.5 hours. The trifluoroacetic acid is distilled off and the residue is partitioned between semisaturated sodium hydrogen carbonate solution and dichloromethane. The phases are separated and the aqueous phase is subjected to extraction with dichloromethane. The combined organic phases are washed with semisaturated sodium hydrogen carbonate solution, dried over potassium carbonate and filtered and the solvent is distilled off.

Yield: 0.37 g of 2-amino-5-(phenylcarbonyl)thiazole (67% of theory) as yellow crystals.

M.p.: 147°–149° C.

$^1$H NMR (400 MHz, DMSO-d$_6$) 7.48–7.53 (m, 2H), 7.57–7.62 (m, 1H), 7.62 (s, 1H), 7.68–7.73 (m, 2H). $^{13}$C NMR (100 MHz, DMSO-d$_6$) 127.1, 128.3, 128.7, 131.7, 138.4, 151.0, 174.9, 185.5.

EXAMPLE 3

N-[5-(Phenylcarbonyl)-1,3,4-thiadiazol-2-yl]-3,3,3-trifluoro-2-hydroxy-2-methylpropanamide Thionyl chloride (80 μl, 1.1 mmol) is added to 3,3,3-trifluoro-2-hydroxy-2-methylpropanoic acid (157 mg, 0.993 mmol) in 5.0 ml of N,N-dimethylacetamide at −20°/−15° C. and the mixture is stirred at −15°/−10° C. for one hour. After adding 2-amino-5-(phenylcarbonyl)-1,3,4-thiadizole (127.7 mg, 0. 622 mmol) and equilibration to room temperature and after the reaction has ended, the reaction mixture is poured into 80 ml of water and subjected to extraction with 3×25 ml of ethyl acetate. The combined organic phases are dried over magnesium sulfate and filtered and the solvent is distilled off. The oil which remains is purified by flash chromatography (eluent: 50% v/v ethyl acetate in petroleum ether (40/60)).

Yield: 160 mg of N-[5-(phenylcarbonyl)-1,3,4-thiadiazol-2-yl]-3,3,3-trifluoro-2-hydroxy-2-methylpropanamide (75% of theory) as beige crystals.

M.p.: 182°–183° C.

$^1$H NMR (400 MHz, DMSO-d$_6$) 1.65 (s, 3H), 7.60–7.65 (m, 2H), 7.62 (bs, 1H), 7.73–7.78 (m, 1H), 8.33–8.37 (m, 2H), 10.8 (bs, 1H). $^{13}$C NMR (100 MHz, DMSO-d$_6$) 19.8, 75.3 (q, $^2J_{C,F}$=29.2 Hz), 125.9 (q, $^1J_{C,F}$=285.8 hz) 128.8, 130.7, 134.3, 134.9, 161.9, 163.6, 169.4, 184.2.

The synthesis of 2-amino-5-(phenylcarbonyl)-1,3,4-thiadiazole is described by G. Werber, F. Buccheri and M. L. Marino, J. Heterocyclic Chem. 12 (1975), 581.

EXAMPLE 4

N-[5-(Phenylsulfonyl)thien-2-yl]-3,3,3-trifluoro-2-hydroxy-2-methylpropanamide

Thionyl chloride (80 μl, 1.1 mmol) is added to 3,3,3-trifluoro-2-hydroxy-2-methylpropanoic acid (170 mg, 1.08 mmol) in 5 ml of N,N-dimethylacetamide at −15°/−10° C. and the mixture is stirred at this temperature for one hour. After adding 2-amino-5-(phenylsulfonyl)thiophene (170 mg, 0.710 mmol) and equilibration to room temperature and after the reaction has ended, the reaction mixture is poured into 200 ml of water and subjected to extraction with 3×100 ml of ethyl acetate. The combined organic phases are dried over magnesium sulfate and filtered and the solvent is distilled off. The orange-colored oil which remains is purified by flash chromatography (eluent: 50% v/v ethyl acetate in petroleum ether (40/60)).

Yield: 202 mg of N-[5-(phenylsulfonyl)thien-2-yl]-3,3,3-trifluoro-2-hydroxy-2-methylpropanamide (75% of theory) as gray crystals.

M.p.: 161°–163° C.

$^1$H NMR (400 MHz, DMSO-d$_6$) 1.57 (s, 3H), 7.11 (d, J=4.2 Hxz, 1H), 7.58–7.70 (m, 5H), 7.90–7.93 (m, 2H). $^{13}$C NMR (100 MHz, DMSO-d$_6$) 19.9, 75.3 (q, $^2J_{C,F}$=29.2 Hz) 114.3, 125.9 (q, $^1J_{C,F}$=285 8 Hz), 126.6, 129.8, 131.4, 132.5, 133.5, 142.6, 147.1, 167.3.

The starting compound is prepared as follows:

5-(Phenylsulfonyl)thiophene-2-carboxylic acid:

A 1.6M solution of n-butyllithium in n-hexane (51.0 ml, 81.3 mmol) is added dropwise to diisopropylamine (11.6 ml, 82.2 mmol) in 150 ml of absolute THF at −78° C. After stirring at −70° C. for 30 minutes, thiophene-2-carboxylic acid (5.00 g, 39.0 mmol) is added and the mixture is held at −78° C. After 60 minutes, diphenyl disulfide (9.39 g, 43.0 mmol) is added and the mixture is stirred at −78° C. for 60 minutes. After equilibration of the reaction mixture to room temperature, it is poured into 400 ml of 1N HCl solution and subjected to extraction with 3×200 ml of dichloromethane. The combined organic phases are dried over magnesium-sulfate and filtered and the solvent is distilled off. The orange-colored oil which remains (14.59 g) is dissolved in 150 ml of methanol, and a solution of Oxone® (113.87 g, 185.22 mmol) in 450 ml of water is added dropwise at 0° C. After equilibration of the reaction mixture to room temperature, stirring is continued for 3 hours. The reaction mixture is subjected to extraction with 3×200 ml of ether. The combined organic phases are washed with 100 ml of 1N HCl solution, dried over magnesium sulfate and filtered and the solvent is distilled off. The yellow crystals which remain (9.76 g) are suspended in dichloromethane. The crystals are filtered off and washed a little with cold dichloromethane.

Yield: 4.80 g of 5-(phenylsulfonyl)thiophene-2-carboxylic acid (46% of theory) as white crystals.

M.p.: 84°–185° C.

$^1$H NMR (400 MHz, DMSO-d$_6$) 7.64–7.69 (m, 2H), 7.71 (d, J=4.0 Hz, 1H), 7.72–7.77 (m, 1H), 7.85 (d, J=4.0 Hz, 1H), 8.00–8.05 (m, 2H). $^{13}$C NMR (100 MHz, DMSO-d$_6$) 127.4, 130.1, 133.4, 134.2, 134.5, 140.7, 142.2, 147.1, 161.8.

tert-Butyl (5-(phenylsulfonyl)thien-2-yl]carbamate:

Triethylamine (0.62 ml, 4.4 mmol) and diphenylphosphoryl azide (0.97 ml, 4.5 mmol) are added to 5-(phenylsulfonyl)thiophene-2-carboxylic acid (1.00 g, 3.7 mmol) in 40 ml of absolute tert-butanol. The reaction mixture is boiled under reflux for 5 hours. The solvent is distilled off. The residue is taken up in ethyl acetate and washed with water. The organic phase is dried over magnesium sulfate and filtered and the solvent is distilled off. The green-black oil which remains is purified by flash chromatography (eluent: 33% v/v ethyl acetate in petroleum ether (40/60)).

Yield: 520 mg of tert-butyl [5-(phenylsulfonyl)thien-2-yl] carbamate (41% of theory) as white crystals.

M.p.: 170°–171° C.

$^1$H NMR (400 MHz, DMSO-d$_6$) 1.47 (s, 9H), 6.53 (d, J=4.3 Hz, 1H), 7.56 d, J=4.3 Hz, 1H), 7.57–7.68 (m, 3H), 7.87–7.92 (m, 2H), 11.13 (bs, 1H). $^{13}$C NMR (100 MHz, DMSO-d$_6$) 28.0, 81.6, 110.2, 126.5, 129.0, 129.7, 133.3 (2×C), 142.9, 150.5, 152.5.

2-Amino-5-(phenylsulfonyl)thiophene:

tert-Butyl [5-(phenylsulfonyl)thien-2-yl]carbamate (0.37 g, 1.1 mmol) is dissolved in 5 ml of trifluoroacetic acid and the solution is stirred at room temperature for 2 hours. The trifluoroacetic acid is distilled off and the residue is partitioned between semisaturated sodium hydrogen carbonate solution and dichloromethane. The phases are separated and the aqueous phase is subjected to extraction with dichloromethane. The combined organic phases are dried over potassium carbonate and filtered and the solvent is distilled off.

Yield: 0.20 g of 2-amino-5-(phenylsulfonyl)thiophene (76% of theory) as pale yellow crystals.

M.p.: 144°–145° C.

$^1$H NMR (400 MHz, DMSO-d$_6$) 5.90 (d, J=4.0 Hz, 1H), 6.81 (bs, 2H), 7.32 (d, J=4.0 Hz, 1H), 7.55–7.65 (m, 3H), 7.79–7.84 (m, 2H). $^{13}$C NMR (100 MHz, DMSO-d$_6$) 104.4, 117.9, 126.1, 129.5, 132.7, 136.5, 143.8, 165.1.

EXAMPLE 5

N-[5-(phenylcarbonyl)-1,3,4-thiadiazol-2-yl]-2-hydroxy -2-methylpropanamide

Thionyl chloride (60 µl, 0.82 mmol) is added to 2-hydroxyisobutyric acid (82.9 mg, 0.796 mmol) in 5.0 ml of N,N-dimethylacetamide at –20°/–15° C. and the mixture is stirred at –15°/–10° C. for one hour. After adding 2-amino-5-(phenylcarbonyl)-1,3,4-thiadiazole (97.5 mg, 0.475 mmol) and equilibrating the reaction mixture to room temperature, it is stirred overnight. The reaction mixture is poured into 75 ml of water and subjected to extraction with 3×25 ml of ethyl acetate. The combined organic phases are dried over magnesium sulfate and filtered and the solvent is distilled off. The oil which remains is purified by flash chromatography (eluent: 33.% v/v ethyl acetate in petroleum ether (40/60)).

Yield: 30.1 mg of N-[5-(phenylcarbonyl)-1,3,4-thiadiazol-2-yl]-2-hydroxy-2-methylpropanamide (22% of theory) as pale yellow crystals.

M.p.: 189°–190° C.

$^1$H NMR (400 MHz, CDCl$_3$) 1.65 (s, 6H), 7.55–7.60 (m, 2H), 7.68–7.73 (m, 1H), 8.41–8.45 (m, 2H). $^{13}$C NMR (100 MHz, CDCl$_3$) 27.6, 74.1, 128.6, 130.9, 134.2, 134.9, 163.4, 164.2, 175.7, 184.0.

EXAMPLE 6

N-[5-(Phenylcarbonyl)-1,3,4-thiadiazol-2-yl]-2-hydroxy-2-methylbutanamide

Thionyl chloride (60 µl, 0.82 mmol) is added to 2-hydroxy-methylbutyric acid (96.0 mg, 0.813 mmol) in 5.0 ml of N,N-dimethylacetamide at –20°/–15° C. and the mixture is stirred at –15°/–10° C. for one hour. After adding 2-amino-5-(phenylcarbonyl)-1,3,4-thiadiazole (102.3 mg, 0.499 mmol) and equilibrating the reaction mixture to room temperature, it is stirred overnight. The reaction mixture is poured into 100 ml of water and subjected to extraction with 3×25 ml of ethyl acetate. The combined organic phases are dried over magnesium sulfate and filtered and the solvent is distilled off. The oil which remains is purified by flash chromatography (eluent: 33% v/v ethyl acetate in petroleum ether (40/60)).

Yield: 20.0 mg of N-[5-(phenylcarbonyl)-1,3,4-thiadiazol-2-yl]-2-hydroxy-2-methylbutanamide (13% of theory) as pale yellow crystals.

$^1$H NMR (400 MHz, CDCl$_3$) 0.98 (t, J=7.4 Hz, 3H), 1.61 (s, 3H), 1.80–1.90 (m, 1H), 2.00–2.10 (m, 1H), 7.55–7.60 (m, 2H), 7.68–7.73 (m, 1H), 8.41–8.45 (m, 2H). $^{13}$C NMR (100 MHz, CDCl$_3$) 7.8, 25.8, 33.3, 76.9, 128.6, 130.9, 134.2, 134.9, 163.3, 164.1, 175.4, 184.0.

EXAMPLE 7

N-[5-(4-Methylphenylsulfonyl)thien-2-yl]-3,3,3-trifluoro-2-hydroxy-2-methylpropanamide Thionyl chloride (70 µl, 1.51 mmol) is added to 3,3,3,-trifluoro-2-hydroxy-2-methylpropanoic acid (140 mg, 0.89 mmol) in 10 ml of N,N-dimethylacetamide at –15°/–10° C. and the mixture is stirred at this temperature for one hour. Subsequently, 2-amino-5-(4-methylphenylsulfonyl) thiophene (145 mg, 0.57 mmol) is added and the reaction mixture is equilibrated to room temperature. After the reaction has ended, the reaction mixture is poured into 200 ml of water and subjected to extraction with 3×100 ml of ethyl acetate. The combined organic phases are dried over magnesian sulfate and filtered and the solvent is distilled off. The brown oil which remains is purified by flash chromatography (eluent: 50% v/v ethyl acetate in petroleum ether (40/60)).

Yield: 111 mg of N-[5-(4-methylphenylsulfonyl)thien-2-yl]-3,3,3-trifluoro-2-hydroxy-2-methylpropanamide (50% of theory) as light brown crystals.

M.p.: 191°–193° C.

$^1$H NMR (400 MHz, DMSO-d$_6$) 1.57 (s, 3H), 2.37 (s, 3H), 7.10 (d, J=4.2 Hz, 1H), 7.41 (d, J=7.9 Hz, 2H), 7.59 (bs, 1H), 7.61 (d, J=4.2 Hz, 1H), 7.79 (d, J=7.9 Hz, 2H).

The following compounds were prepared analogously:

EXAMPLE 8

N-[5-(4-Chlorophenylsulfonyl)-thien-2-yl]-3,3,3-trifluoro-2-hydroxy-2-methylpropanamide $^1$H NMR (400 MHz, DMSO-d$_6$) 1.58 (s, 3H), 7.13 (d, J=4.0 Hz, 1H), 7.66–7.70 (m, 3H), 7.90–7.93 (m, 2H).

EXAMPLE 9

N-[5-(4-Fluorophenylsulfonyl)-thien-2-yl]-3,3,3-trifluoro-2-hydroxy-2-methylpropanamide $^1$H NMR (400 MHz, DMSO-$d_6$) 1.58 (s, 3H), 7.12 (d, J=4.2 Hz, 1H), 7.41–7.46 (m, 2H), 7.60 (s, 1H), 7.67 (d, J=4.2 Hz, 1H), 7.96 (m, 2H), 8.01 (m, 2H).

EXAMPLE 10

N-[5-(2-Thienylsulfonyl)-2-thienyl]-3,3,3-trifluoro-2-hydroxy-2-methylpropanamide $^1$H NMR (400 MHz, CDCl$_3$) 1.71 (s, 3H), 6.70 (d, J=4.2 Hz, 1H), 7.03 (dd, J=4.9, 3.8 Hz, 1H), 7.50 (d, J=4.2 Hz, 1H), 7.59 (dd, J=5.0, 1.3 Hz, 1H), 7.64 (dd, J=3.9, 1.3 Hz, 1H), 9.68 (bs, 1H).

$^{13}$C NMR (100 MHz, CDCl$_3$) 20.2, 75.6 (q, $^2J_{C,F}$=30.2 Hz), 112.9, 123.6 (q, $^1J_{C,F}$=285.8 Hz), 127.9, 131.4, 133.0, 133.7, 133.9, 143.7, 145.9, 165.6.

EXAMPLE 11

N-[5-pyridyl(2-Pyridylsulfonyl)-2-thienyl]-3,3,3-trifluoro-2-hydroxy-2-methylpropanamide $^1$H NMR (400 MHz, CDCl$_3$) 1.69 (s, 3 H), 6.79 (d, J=4.0 Hz), 7.43–7.47 (m, 1 H), 7.57 (d, J=4.0 Hz), 7.90 (td, J=8.0, 1.2 Hz, 1H), 8.07 (d, J=8.0 Hz, 1 H), 8.59–8.62 (m, 1H), 10.11 (bs, 1H).

EXAMPLE 12

(–)-N-[5-(phenylsulfonyl)thien-2-yl]-3,3,3-trifluor-2-hydroxy-2-methylpropanamide Triethyl amine (0.81 ml, 5.81 mmol) and a few crystals N,N-dimethyl-4-amino-pyridine are added to N-[5-(phenylsulfonyl)-thien-2-yl]-3,3,3-trifluor-2-hydroxy-2-methylpropanamide (2.00 g, 5.27 mmol) in 100 ml of dichloromethane at 0° C. After adding (1S)-(–)-camphane acid chloride (1.26 g, 5.81 mmol) in 20 ml dichloromethane the reaction mixture is equilibrated to room temperature. After the reaction has ended the reaction mixture is poured into 200 ml of water and subjected to extraction with 2×50 ml of dichloromethane. The combined organic phases are dried over magnesium sulfate and filtered and the solvent is distilled off. The mixture of diastereomeres (gray foam, 3.06 g) is purified by flash chromatography (eluent: 9% v/v diethyl ether in dichloromethane). The camphanic acid ester which elutes first is isolated as a white foam (0.74 g, Yield: 25% of theory).

$^1$H NMR (400 MHz, CDCl$_3$) 1.01 (s, 3H), 1.07 (s, 3H), 1.11 (s, 3H), 1.71 (ddd, J=13.3, 9.3, 4.2 Hz, 1H), 1.95 (ddd, J=13.3, 10.8, 4.6 Hz, 1H), 2.03 (s, 3 H), 2.12 (ddd, J=13.6, 9.3, 4.5 Hz, 1H), 2.43 (ddd, J=13.6, 10.8, 4.2 Hz, 1H), 6.75 (d, J=4.2 Hz, 1H), 7.45–7.57 (m, 4 H), 7.91–7.95 (m, 2 H), 9.27 (bs, 1H). $^{13}$C NMR (100 MHz, CDCl$_3$) 9.55, 16.42, 16.50, 16.55, 28.71, 30.79, 54.58, 54.95, 81.62 (q, $^2J_{C,F}$= 30.8 Hz), 90.63, 113.38, 122.36 (q, $^1J_{C,F}$=285.8 Hz), 127.13, 129.32, 131.35, 133.18, 134.36, 142.34, 145.54, 160.93, 164.67, 177.61.

Optical purity:>99% de (Chiral HPLC, Chiracel OD-H column, 10% v/v ethanol in hexane, flow rate 1.0 ml/min).

A 2M solution of NaOH (0.60 ml, 1.2 mmol) is added to the first eluting camphanic acid ester (0.65 g, 1.16 mmol) in 30 ml of methanol at room temperature. After the reaction has ended the solvent is distilled off. The remaining oil is dissolved in 250 ml of dichloromethane and the solution is poured into 250 ml of water and is subjected to extraction with 3×100 ml of dichloromethane. The combined organic phases are dried over magnesium sulfate and filtered and the solvent is distilled off. The remaining white crystals are recrystallised from hexane/ethyl acetate.

Yield: 340 mg of (–)-N-[5-(Phenylsulfonyl)thien-2-yl]-3, 3,3-trifluor-2-hydroxy-2-methylpropanamide (77% of theory) as white crystals.

M.p.: 189°–190° C., $[\alpha]^{20}_D$=–46.5° (c 0.94, methanol), optical purity:>99% ee (chiral HPLC, Chiracel OD-H column, 10% vv ehtanol in hexane, flow rate 1.0 ml/min)

$^1$H NMR and $^{13}$C NMR data are identical to those of the racemic material.

Example A

Effects on the bladder muscle in vitro

The effect of the compounds according to the invention on the bladder muscle can be demonstrated in specifically developed in vitro experiments as described below. In these experiments, the IC$_{50}$ value denotes the concentration of a substance which reduces contraction by 50%.

Male albino guinea pigs weighing about 400 g are killed painlessly by a blow to the neck and quickly exsanguinated. The abdominal cavity is opened and the bladder is carefully resectioned. It is placed in a Petri dish filled with Krebs solution, and surrounding connective and fatty tissue is removed. Two horizontal strips of tissue are prepared. With the aid of two threads which are attached to both ends of the strips of tissue, the strips are suspended in an organ bath. They are fastened at the bottom to a hook and at the top to an electric force transducer which is able to measure precisely contractions of 0–10 g in strength. The measured contractions are amplified by means of a bridge amplifier and are recorded with a thermal plotter. The signals obtained can also be integrated electronically on another plotter channel in order to quantify in-phase contractions.

The organ baths are filled with Krebs solution at 37° C. through which an $O_2/CO_2$ mixture is bubbled thoroughly and which has the following composition (mmol/l): NaCl 118.4; KCl 4.7; CaCl$_2$ 2.5; KH$_2$PO$_4$ 1.2; MgSO$_4$ 1.2; NaHCO$_3$ 25; glucose 11.

The strips are stretched with a basic tone of about 0.5 g. After an equilibration time of about 30 minutes, one of the two strips is stimulated electrically every minute using built-in electrodes (period of stimulation 2 seconds, 30 Hz, 0.5 ms pulse width, 10 volts) in order to trigger short-term contractions. The other strip is made to exert in-phase contraction by depolarization (addition of 15 nM KCl to the organ bath). Both the contractions triggered by electrical stimulation and those initiated by depolarization and occurring in the strips of bladder muscle quickly reach a plateau. As soon as this plateau is reached ("100% value"), the test substance is added to the organ bath, initially at 10w concentrations, for example 10$^{-8}$M, and then in increasing doses at regular intervals, until the contractions reduce or the final concentration of 10$^{-4}$M is reached. Each test substance is tested 2–4 times in this way.

For purposes of evaluation, the height of the contractions registered on the plotter paper is measured for each experiment after the action of each test concentration added. The IC$_{50}$ value can be calculated in this way in relation to the original height of contractions before the addition of substance (100%). All of the IC$_{50}$ values are shown in column A of Table 1.

Example B

Effects on vessel muscle in vitro
Aorta rings

Male rats weighing about 300 g are killed painlessly by a blow to the neck and quickly exsanguinated. The thoracic cavity is opened and the aorta is carefully resectioned. It is placed in a Petri dish filled with Krebs solution, and surrounding connective and fatty tissue is removed. Two rings are prepared. The rings are each suspended in an organ bath. They are attached at the bottom to a hook and at the top to an electrical force transducer which is able to measure precisely contractions of 0–10 grams in strength. The measured contractions are amplified by means of a bridge amplifier and recorded with a thermal plotter.

The organ baths are filled with Krebs solution at 37° C. through which an $O_2/CO_2$ mixture is bubbled thoroughly and which has the following composition (mmol/l): NaCl 118.4; KCl 4.7; $CaCl_2$ 2.5; $KH_2PO_4$ 1.2; $MgSO_4$ 1.2; $NaHCO_3$ 25; glucose 11.

The rings are stretched with a basic tone of about 0.5 g. After an equilibration time of about 30 minutes, the rings are caused to undergo contraction by depolarization (addition of 25 mM KCl to the organ bath). The contractions of the rings of aorta, triggered by the depolarization, quickly reach a plateau. As soon as this plateau is reached ("100% value"), the test substance is added to the organ bath, initially at low concentrations, for example $10^{-8}M$, and then in increasing doses at regular intervals, until the contractions reduce or the final concentration of $10^{-4}M$ is reached. Each test substance is tested 2–4 times in this way.

For purposes of evaluation, the height of the contractions registered on the plotter paper is measured for each experiment after the action of each test concentration added. The $IC_{50}$ value can be calculated in this way in relation to the original height of contractions before the addition of substance (100%). $IC_{50}$ values are shown in column B of Table 1.

Example C:

Effects on blood pressure in vivo
Conscious rat

Male Sprague-Dawley rats (Charles River, Sulzfeld, Germany) weighing about 400 g had a catheter implanted in the carotid artery under sterile conditions before the beginning of the experiment, in order to enable continual measurement of the arterial blood pressure using a customary pressure transducer (e.g. Statham P23d). The rats were fasted overnight before the day of the experiment.

On the day of experiment, the rats were brought into the laboratory and their blood pressure and heart rate was recorded over about 30 minutes. The test substances, suspended in 0.5% methylcellulose, were then administered perorally via a stomach tube (volume: 3 ml/kg of body weight) and blood pressure and heart rate were measured over the next 6 hours. The percentage changes in the measured values in relation to the initial values were calculated and were determined for groups of 3–4 similarly treated animals. The results are shown in column C of Table 1.

TABLE 1

| | A<br>$IC_{50}$ | B<br>$IC_{50}$ | | Dose | C<br>Reduction in diastolic pressure<br>% of initial value | | | |
|---|---|---|---|---|---|---|---|---|
| Compd. | mol/l | mol/l | Select. | mg/kg | 15 | 30 | 60 | 120 min. |
| 1 | $1.0 \times 10^{-4}$ | $2.5 \times 10^{-6}$ | 0.025 | 6 | | 3 | 2 | 4 |
| 2 | $1.0 \times 10^{-4}$ | $2.0 \times 10^{-5}$ | 0.2 | 6 | 2 | 8 | 5 | |
| 3 | $5.0 \times 10^{-5}$ | $1.0 \times 10^{-5}$ | 0.2 | 6 | | 3 | 2 | 4 |
| 4 | $1.7 \times 10^{-6}$ | $1.2 \times 10^{-6}$ | 0.7 | 6 | 1 | 5 | 4 | 6 |
| | | | | 18 | 0 | 8 | 10 | 15 |
| V | $1.0 \times 10^{-6}$ | $6.5 \times 10^{-8}$ | 0.065 | 1 | 53 | 49 | 40 | 26 |

Table 1: Relaxant effect of the abovementioned substances on bladder strips (column A) and rings of aorta (columns B) in vitro. The ratio $IC_{50}$ bladder:$IC_{50}$ aorta gives the selectivity. Column C lists the hypotensive effects in vivo 15, 30, 60 and 120 minutes after peroral administration of substance. Corresponding values for the reference substance (compound V) cromakalim are shown for comparison.

What is claimed is:

1. A heterocyclic amide of the formula I

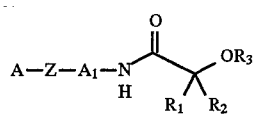

in which

A is an aromatic or S- or N-heteroaromatic ring having 5–10 carbon atoms which can be unsubstituted or mono- or polysubstituted by straight-chain or branched $C_1$–$C_4$alkyl, $C_1$–$C_4$ alkoxy, hydroxyl, halogen or $CF_3$, $CF_3CF_2$, Z is a radical C=O, SO or $SO_2$, $A_1$ is a heteroaromatic system of the formula IIa–IIc

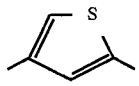

IIa

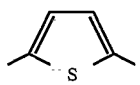

IIb

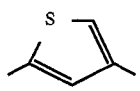

IIc or a heteroaromatic system of the formula IIIa–IIIc

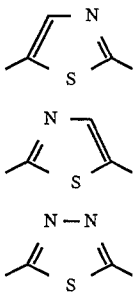

IIIa

IIIb

IIIc $R_1$ and $R_2$ independently of one another are H, straight-chain or branched $(C_1-C_4)$-alkyl or fluorinated alkyl, and $R_3$ is H, straight-chain or branched $(C_1-C_4)$-alkyl, acetyl, alkylacetyl or a group which can be eliminated under physiological conditions.

2. A heterocyclic amide of the formula I as claimed in claim 1, in which
A is an unsubstituted phenyl radical or a phenyl radical which is substituted by halogen, $CF_3$ or $CF_3CF_2$, or is a 2- or 3-thienyl radical,
Z is a group C=O or $SO_2$,
$A_1$ is a heteroaromatic system of the formula IIb, IIIb or IIIc,
$R_1$ and $R_2$ independently of one another are a straight-chain or branched alkyl radical having 1–4 carbon atoms or the radical $CF_3$,
and $R_3$ is H or a straight-chain or branched alkyl radical having 1–4 carbon atoms.

3. A heterocyclic amide of the formula I as claimed in claim 1, in which
A is an unsubstituted phenyl radical or a phenyl radical which is substituted by halogen, $CF_3$ or $CF_3CF_2$, or is a 2- or 3-thienyl radical,
Z is a group C=O or $SO_2$,
$A_1$ is a heteroaromatic system of the formula IIb,
$R_1$ is methyl,
$R_2$ is $CF_3$
and $R_3$ is H.

4. N-[5-(Phenylsulfonyl)-thien-2-yl]-3,3,3-tri-fluoro-2-hydroxy-2-methylpropanamide.

5. A heterocyclic amide as claimed in one of claims 1 to 4, wherein the compound is present in its enantiomeric pure form.

6. A heterocyclic amide as claimed in one of claims 1 to 4, wherein the compound is present as a mixture of its optical isomers.

7. A process for the preparation of a compound of the formula I

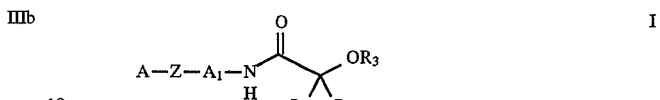

which comprises coupling a compound of the formula IV

with the aid of known coupling reagents, with a compound of the formula V

and, if appropriate, separating the resulting mixture of optical isomers into the enantiomers.

8. The process as claimed in claim 7, wherein the compound of the formula V is employed in an optically active form.

9. A pharmaceutical preparation comprising a heterocyclic amide of the formula I as claimed in claim 1 together with customary pharmaceutical auxiliaries and/or excipients and/or diluents.

10. A method for treating disorders or diseases which can be cured or ameliorated by exerting influence on potassium channels which comprises administering to a patient in need of such treatment a heterocyclic amide of the Formula I as claimed in claim 1.

11. A method for treating disorders and diseases of the bladder and of the efferent urinary tract passages which comprises administering to a patient in need of such treatment a heterocyclic amide of the Formula I as claimed in claim 1.

12. A method for treating incontinence which comprises administering to a patient in neea of such treatment a heterocyclic amide of the Formula I as claimed in claim 1.

* * * * *